(12) United States Patent  
Wariar et al.

(10) Patent No.: US 7,424,321 B2  
(45) Date of Patent: Sep. 9, 2008

(54) SYSTEMS AND METHODS FOR MULTI-AXIS CARDIAC VIBRATION MEASUREMENTS

(75) Inventors: Ramesh Wariar, Blaine, MN (US); Krzysztof Z. Siejko, Maple Grove, MN (US); Gerrard M. Carlson, Champlin, MN (US); Jeffrey E. Stahmann, Ramsey, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 347 days.

(21) Appl. No.: 11/135,985

(22) Filed: May 24, 2005

(65) Prior Publication Data

US 2006/0270939 A1 Nov. 30, 2006

(51) Int. Cl.  
*A61B 5/04* (2006.01)  
*A61B 5/025* (2006.01)  
*A61B 5/0225* (2006.01)

(52) U.S. Cl. .................. 600/514; 600/493; 600/528

(58) Field of Classification Search .............. 600/493, 600/514, 528, 586; 607/17, 18  
See application file for complete search history.

(56) References Cited

U.S. PATENT DOCUMENTS

| | | | |
|---|---|---|---|
| 4,094,308 A | 6/1978 | Cormier | |
| 4,289,141 A | 9/1981 | Cormier | |
| 4,428,380 A | 1/1984 | Wong et al. | |
| 4,446,872 A | 5/1984 | Marsoner et al. | |
| 4,548,204 A | 10/1985 | Groch et al. | |
| 4,628,939 A | 12/1986 | Little et al. | |
| 4,649,930 A | 3/1987 | Groch et al. | |
| 4,763,646 A | 8/1988 | Lekholm | |
| 4,905,706 A | 3/1990 | Duff et al. | |
| 4,915,113 A | 4/1990 | Holman | |
| 4,967,760 A | 11/1990 | Bennett et al. | |
| 4,981,139 A | 1/1991 | Pfohl | |
| 4,989,611 A | 2/1991 | Zanetti et al. | |
| 5,010,889 A | 4/1991 | Bredesen et al. | |

(Continued)

FOREIGN PATENT DOCUMENTS

EP 0762908 B1 3/1997

(Continued)

OTHER PUBLICATIONS

"International Search Report and Written Opinion for Application PCT/US2006/019729, Mailed Nov. 17, 2006", 11 Pages.

(Continued)

*Primary Examiner*—Carl H. Layno  
*Assistant Examiner*—Tammie K. Heller  
(74) *Attorney, Agent, or Firm*—Schwegman, Lundberg & Wuessner, P.A.

(57) ABSTRACT

A system to monitor heart sounds, such as to detect a worsening condition of heart failure decompensation. The system comprises a medical device that includes an implantable multi-axis heart sound sensor, operable to produce, for each of at least two nonparallel axes, an electrical signal representative of at least one heart sound, the heart sound associated with mechanical activity of a patient's heart. The device further includes a controller circuit coupled to the heart sound sensor. The controller circuit measures components of the heart sound that respectively correspond to each of the axes.

33 Claims, 5 Drawing Sheets

U.S. PATENT DOCUMENTS

| | | |
|---|---|---|
| 5,025,809 A | 6/1991 | Johnson et al. |
| 5,159,932 A | 11/1992 | Zanetti et al. |
| 5,218,969 A | 6/1993 | Bredesen et al. |
| 5,301,679 A | 4/1994 | Taylor |
| 5,337,752 A | 8/1994 | Reeves |
| 5,472,453 A | 12/1995 | Alt |
| 5,496,361 A | 3/1996 | Moberg et al. |
| 5,544,661 A | 8/1996 | Davis et al. |
| 5,554,177 A | 9/1996 | Kieval et al. |
| 5,593,431 A | 1/1997 | Sheldon |
| 5,674,256 A | 10/1997 | Carlson |
| 5,685,317 A | 11/1997 | Sjostrom |
| 5,687,738 A | 11/1997 | Shapiro et al. |
| 5,697,375 A | 12/1997 | Hickey |
| 5,700,283 A | 12/1997 | Salo |
| 5,725,562 A | 3/1998 | Sheldon |
| 5,792,195 A | 8/1998 | Carlson et al. |
| 5,836,987 A | 11/1998 | Baumann et al. |
| 5,860,933 A | 1/1999 | Don Michael |
| 5,911,738 A | 6/1999 | Sikorski et al. |
| 5,935,081 A | 8/1999 | Kadhiresan |
| 5,991,661 A | 11/1999 | Park et al. |
| 6,002,777 A | 12/1999 | Grasfield et al. |
| 6,022,963 A | 2/2000 | McGall et al. |
| 6,044,297 A | 3/2000 | Sheldon et al. |
| 6,044,298 A | 3/2000 | Salo et al. |
| 6,044,299 A | 3/2000 | Nilsson |
| 6,053,872 A | 4/2000 | Mohler |
| 6,058,329 A | 5/2000 | Salo et al. |
| 6,064,910 A | 5/2000 | Andersson et al. |
| 6,076,015 A | 6/2000 | Hartley et al. |
| 6,077,227 A | 6/2000 | Miesel et al. |
| 6,152,884 A | 11/2000 | Bjorgaas |
| 6,193,668 B1 | 2/2001 | Chassaing et al. |
| 6,208,900 B1 | 3/2001 | Ecker et al. |
| 6,298,269 B1 | 10/2001 | Sweeney |
| 6,351,672 B1 | 2/2002 | Park et al. |
| 6,366,811 B1 | 4/2002 | Carlson |
| 6,368,283 B1 | 4/2002 | Xu et al. |
| 6,409,675 B1 | 6/2002 | Turcott |
| 6,415,033 B1 | 7/2002 | Halleck et al. |
| 6,440,082 B1 | 8/2002 | Joo et al. |
| 6,466,821 B1 | 10/2002 | Pianca et al. |
| 6,477,406 B1 | 11/2002 | Turcott |
| 6,478,746 B2 | 11/2002 | Chassaing et al. |
| 6,520,924 B2 | 2/2003 | Lee |
| 6,527,729 B1 | 3/2003 | Turcott |
| 6,567,700 B1 | 5/2003 | Turcott et al. |
| 6,625,493 B2 | 9/2003 | Kroll et al. |
| 6,626,842 B2 | 9/2003 | Oka |
| 6,643,548 B1 | 11/2003 | Mai et al. |
| 6,650,940 B1 | 11/2003 | Zhu et al. |
| 6,658,292 B2 | 12/2003 | Kroll et al. |
| 6,665,564 B2 | 12/2003 | Lincoln et al. |
| 6,795,732 B2 | 9/2004 | Stadler et al. |
| 6,810,287 B2 | 10/2004 | Zhu et al. |
| 6,824,519 B2 | 11/2004 | Narimatsu et al. |
| 6,845,263 B2 | 1/2005 | Kawaguchi |
| 6,885,889 B2 | 4/2005 | Chinchoy |
| 7,115,096 B2 | 10/2006 | Siejko et al. |
| 7,123,962 B2 | 10/2006 | Siejko et al. |
| 7,248,923 B2 | 7/2007 | Maile et al. |
| 2002/0001390 A1 | 1/2002 | Kawaguchi |
| 2002/0035337 A1 | 3/2002 | Oka |
| 2002/0082645 A1 | 6/2002 | Sweeney |
| 2002/0107450 A1 | 8/2002 | Ogura |
| 2002/0147401 A1 | 10/2002 | Oka |
| 2002/0151812 A1 | 10/2002 | Scheiner et al. |
| 2002/0151938 A1 | 10/2002 | Corbucci |
| 2003/0055352 A1 | 3/2003 | Hayek et al. |
| 2003/0069608 A1 | 4/2003 | Sweeney |
| 2003/0072458 A1 | 4/2003 | Halleck et al. |
| 2003/0078624 A1 | 4/2003 | Carlson et al. |
| 2003/0093002 A1 | 5/2003 | Kuo |
| 2003/0093003 A1 | 5/2003 | Watrous et al. |
| 2003/0105497 A1* | 6/2003 | Zhu et al. .................. 607/17 |
| 2003/0120159 A1 | 6/2003 | Mohler |
| 2003/0158492 A1 | 8/2003 | Sheldon et al. |
| 2003/0176896 A1 | 9/2003 | Lincoln et al. |
| 2003/0208240 A1 | 11/2003 | Pastore et al. |
| 2003/0216620 A1 | 11/2003 | Jain et al. |
| 2003/0229289 A1 | 12/2003 | Mohler |
| 2004/0024423 A1 | 2/2004 | Lincoln et al. |
| 2004/0039295 A1 | 2/2004 | Olbrich et al. |
| 2004/0039419 A1 | 2/2004 | Stickney et al. |
| 2004/0039420 A1 | 2/2004 | Jayne et al. |
| 2004/0064056 A1 | 4/2004 | Ogura |
| 2004/0073093 A1 | 4/2004 | Hatlestad |
| 2004/0106960 A1 | 6/2004 | Siejko et al. |
| 2004/0106961 A1 | 6/2004 | Siejko et al. |
| 2004/0122484 A1 | 6/2004 | Hatlestad et al. |
| 2004/0127792 A1 | 7/2004 | Siejko et al. |
| 2004/0138572 A1 | 7/2004 | Thiagarajan |
| 2004/0167417 A1 | 8/2004 | Schulhauser et al. |
| 2004/0215264 A1 | 10/2004 | Van Bentem |
| 2004/0225332 A1 | 11/2004 | Gebhardt et al. |
| 2004/0236239 A1 | 11/2004 | Murray et al. |
| 2004/0254481 A1 | 12/2004 | Brodnick |
| 2004/0267147 A1 | 12/2004 | Sullivan |
| 2004/0267148 A1 | 12/2004 | Arand et al. |
| 2005/0027323 A1 | 2/2005 | Mulligan et al. |
| 2005/0033190 A1 | 2/2005 | Bauer |
| 2005/0060001 A1 | 3/2005 | Singhal et al. |
| 2005/0102001 A1 | 5/2005 | Maile et al. |
| 2005/0148896 A1 | 7/2005 | Siejko et al. |
| 2005/0148897 A1 | 7/2005 | Cho et al. |
| 2005/0149136 A1 | 7/2005 | Siejko et al. |
| 2006/0020294 A1 | 1/2006 | Brockway et al. |
| 2006/0020295 A1 | 1/2006 | Brockway et al. |
| 2006/0025699 A1 | 2/2006 | Maile et al. |
| 2006/0161070 A1 | 7/2006 | Siejko et al. |
| 2006/0282000 A1 | 12/2006 | Zhang et al. |

FOREIGN PATENT DOCUMENTS

| | | |
|---|---|---|
| EP | 1179317 A2 | 2/2002 |
| EP | 1247485 A1 | 10/2002 |
| WO | WO-0156651 A1 | 8/2001 |
| WO | WO-2006127594 A2 | 11/2006 |

OTHER PUBLICATIONS

Kinderman, Michael, et al., "Optimizing the AV Delay in DDD Pacemaker Patients with High Degree AV Block: Mitral Valve Doppler Versus Impedance Cardiography", *Pace*, vol. 20, (Oct. 1997), 2453-2462.

Leonelli, Fabio M., et al., "Systolic and Diastolic Effects of Variable Atroventricular Delay and Patients with Complete Hear Block and Normal Ventricular Function", *Amer. J-Cardiology*, vol. 80, (Aug. 1, 1997), 294-298.

Pinchak, Alfred C., et al., "Multiaxial Accelerometers", *Encyclopedia of Medical Devices and Instrumentation, vol. 1, Department of Electrical and Computer Engineering*, (1988), 12 Pages.

Ritter, P., et al., "New Method for Determining the Optimal Atrio-Ventricular Delay in Patients Place in DDD Mode for Complete Atrio-Ventricular Block", *NASPE abstract #237*, (1995), 885.

Siejko, Krzysztof Z., et al., "A Third Heart Sound Activity Index for Heart Failure Monitoring", U.S. Appl. No. 11/465,878, filed Aug. 21, 2006, 35 Pages.

"U.S. Appl. No. 10/334,694, Response filed Dec. 3, 2007 to Final Office Action mailed Oct. 1, 2007", 21 pgs.

"U.S. Appl. No. 10/334,694 Non-Final Office Action Nov. 27, 2006", 14 pgs.

"U.S. Appl. No. 10/334,694 Non-Final Office Action Apr. 20, 2007", 28 pgs.

"U.S. Appl. No. 10/334,694 Response to Non-Final Office Action filed Feb. 27, 2007", 28 pgs.

"U.S. Appl. No. 10/334,694 Response to Non-Final Office Action filed Jul. 20, 2007", 18 Pages.

"U.S. Appl. No. 10/703,175, Final Office Action mailed Oct. 12, 2006", 10 pgs.

"U.S. Appl. No. 10/703,175, Non-Final Office Action mailed May 10, 2006", 13 pgs.

"U.S. Appl. No. 10/703,175, Notice of Allowance mailed Mar. 19, 2007", 6 pgs.

"U.S. Appl. No. 10/703,175, Response file Dec. 12, 2006 to Final Office Action mailed Oct. 12, 2006", 21 pgs.

"U.S. Appl. No. 10/703,175, Response filed Aug. 9, 2006 to Non-Final Office Action mailed May 10, 2006", 20 pgs.

"U.S. Appl. No. 10/746,874 Notice of Allowance mailed May 19, 2006", 13 pgs.

"U.S. Appl. No. 10/865,498 Non-Final Office Action mailed Sep. 11, 2006", 11 pgs.

"U.S. Appl. No. 10/865,498 Notice Of Allowance mailed Dec. 6, 2006", 12 pgs.

"U.S. Appl. No. 10/865,498 Response to Non-Final Office Action filed Oct. 24, 2006", 23 pgs.

"U.S. Appl. No. 10/900,570, Non-Final Office Action mailed Jan. 10, 2008", 4 pgs.

"U.S. Appl. No. 10/334,694 Final Office Action mailed Oct. 1, 2007", 14 pgs.

Breithardt, O. A., et al., "Acute effects of cardiac resynchronization therapy on functional mitral regurgitation in advanced systolic heart failure", *Journal of the American College of Cardiology*, 41(5), (May 21, 2003), 765-70.

Carabello, B. A., "Mitral valve disease", *Current Problems in Cardiology*, 18(7), (Jul. 1993), 423-78.

Fenster, M. S., et al., "Mitral regurgitation: an overview", *Curr Probl Cardiol.*, 20(4), (Apr. 1995), 193-280.

Say, O., et al., "Classification of heart sounds by using wavelet transform", *24th Annual Conference and the Annual Fall Meeting of the Biomedical Engineering Society] EMBS/BMES Conference*, vol. 2, (2002), 128-129.

Zin, Z. M., et al., "Wavelet analysis and classification of Mitral regurgitation and normal heart sounds based on artificial neural networks", *Seventh International Symposium on Signal Processing and its Applications*, vol. 2, (Jul. 1-4, 2003), 619-620.

* cited by examiner

SYSTEMS AND METHODS FOR MULTI-AXIS CARDIAC VIBRATION MEASUREMENTS

CROSS-REFERENCE TO RELATED APPLICATIONS

This application is related to the following co-pending, commonly assigned U.S. patent application Ser. No. 10/900,570, entitled "DETERMINING A PATIENT'S POSTURE FROM MECHANICAL VIBRATIONS OF THE HEART," filed on Jul. 28, 2004, Ser. No. 10/703,175, entitled "A DUAL USE SENSOR FOR RATE RESPONSIVE PACING AND HEART SOUND MONITORING," filed on Nov. 6, 2003, Ser. No. 10/334,694 entitled "METHOD AND APPARATUS FOR MONITORING OF DIASTOLIC HEMODYNAMICS," filed on Dec. 30, 2002, and Ser. No. 10/746,874 entitled "A THIRD HEART SOUND ACTIVITY INDEX FOR HEART FAILURE MONITORING," filed on Dec. 24, 2003 which are hereby incorporated by reference.

TECHNICAL FIELD

The field generally relates to implantable medical devices and, in particular, but not by way of limitation, to systems and methods for monitoring the mechanical functions of the heart.

BACKGROUND

Implantable medical devices (IMDs) are devices designed to be implanted into a patient. Some examples of these devices include cardiac function management (CFM) devices such as implantable pacemakers, implantable cardioverter defibrillators (ICDs), cardiac resynchronization devices, and devices that include a combination of such capabilities. The devices are typically used to treat patients using electrical therapy and to aid a physician or caregiver in patient diagnosis through internal monitoring of a patient's condition. The devices may include electrodes in communication with sense amplifiers to monitor electrical heart activity within a patient, and often include sensors to monitor other internal patient parameters. Other examples of implantable medical devices include implantable insulin pumps or devices implanted to administer drugs to a patient.

Heart sounds are associated with mechanical vibrations from activity of a patient's heart and the flow of blood through the heart. Heart sounds recur with each cardiac cycle and are separated and classified according to the activity associated with the vibration. The first heart sound (S1) is the vibrational sound made by the heart during tensing of the mitral valve. The second heart sound (S2) marks the beginning of diastole. The third heart sound (S3) and fourth heart sound (S4) are related to filling pressures of the left ventricle during diastole.

SUMMARY

This document discusses, among other things, systems and methods for monitoring heart sounds. One system embodiment includes a medical device which in turn includes an implantable multi-axis heart sound sensor, operable to produce, for each of at least two nonparallel axes, an electrical signal representative of at least one heart sound, the heart sound associated with mechanical activity of a patient's heart. The device also includes a controller circuit, coupled to the heart sound sensor, the controller circuit operable to measure components of the heart sound that respectively correspond to each of the axes.

One method embodiment includes sensing at least one heart sound, which is representative of mechanical activity of a patient's heart, along at least two nonparallel axes, the sensing including using an implantable medical device, and measuring components of the heart sound corresponding to the axes.

This summary is intended to provide an overview of the subject matter of the present patent application. It is not intended to provide an exclusive or exhaustive explanation of the invention. The detailed description is included to provide further information about the subject matter of the present patent application.

DETAILED DESCRIPTION

In the following detailed description, reference is made to the accompanying drawings which form a part hereof, and specific embodiments in which the invention may be practiced are shown by way of illustration. It is to be understood that other embodiments may be used and structural or logical changes may be made without departing from the scope of the present invention.

Monitoring of heart sounds aids caregivers in detecting overall progression of heart disease. For example, for detection of ischemia, an increase in ventricular chamber stiffness and an increase in the degree of restrictive filling are correlated to an increase in loudness of S3 heart sounds. Conversely, because ischemia is associated with a decrease in ventricular chamber contractility, ischemia is correlated to a decrease in the loudness of the S1 heart sound.

Implantable medical devices (IMDs) can include sensors to assist caregivers in monitoring internal patient parameters such as heart sounds. Typically, a heart sound sensor is an accelerometer monitoring heart sound vibrations along a single axis. Monitoring along only one axis may miss sensing additional heart sound information because the vibrations may radiate in multiple directions. Additionally, it is possible that heart sound information may not contain any information along the measurement axis of a single axis sensor. The present inventors have recognized a need for improved measurement of heart sounds.

Figure 1:
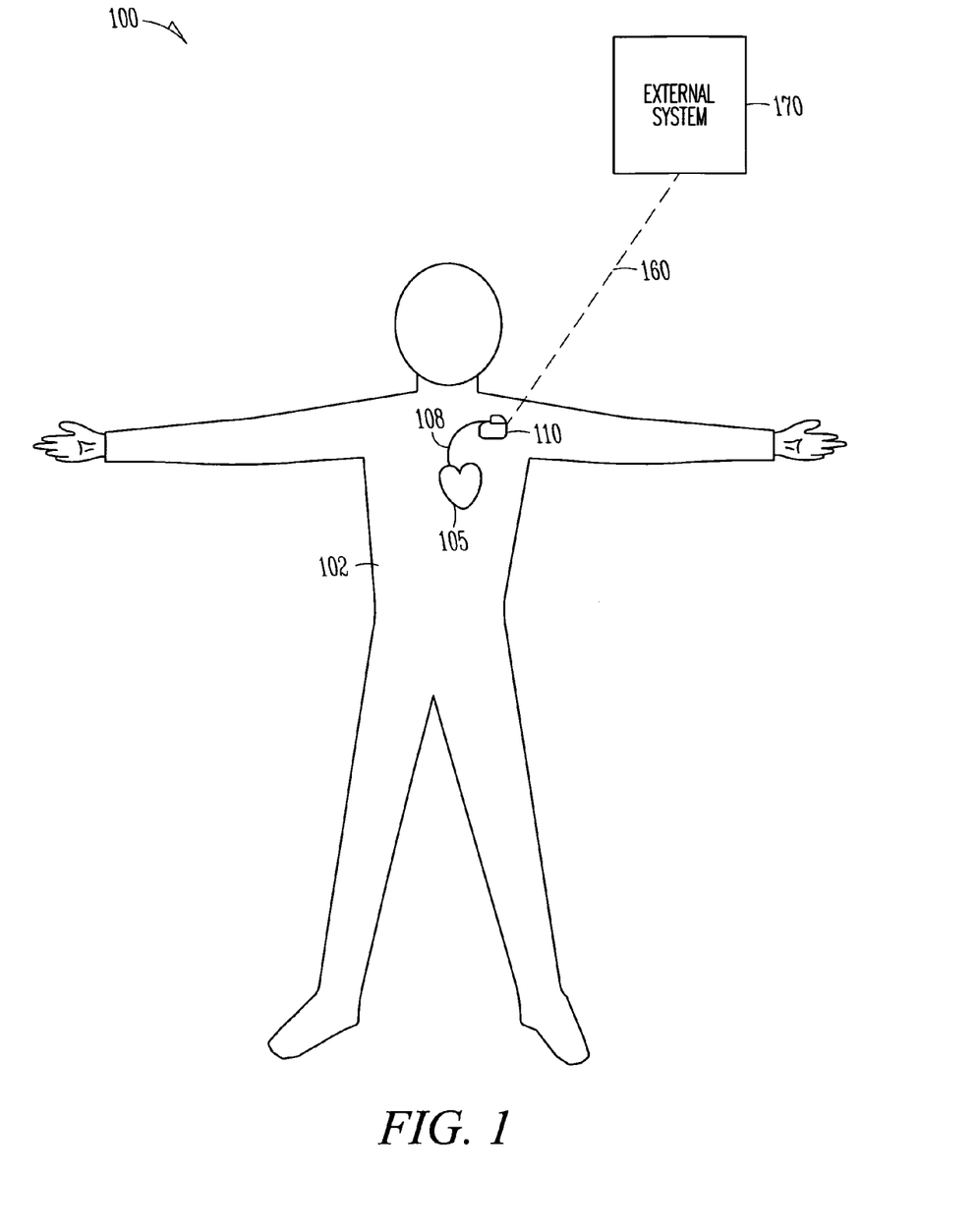
FIG. 1 illustrates an embodiment of a system that uses an implantable medical device.

The present application discusses, among other things, systems and methods for monitoring heart sounds. FIG. 1 illustrates an embodiment of a system 100 that uses an IMD 110. The system 100 shown is one embodiment of portions of a system 100 used to treat a cardiac arrhythmia or otherwise improve heart function. A pulse generator (PG) or other IMD 110 is coupled by a cardiac lead 108, or additional leads, to a heart 105 of a patient 102. Examples of IMD 110 include, without limitation, a pacer, a defibrillator, a cardiac resynchronization therapy (CRT) device, or a combination of such devices. System 100 also includes an IMD programmer or other external system 170 that provides wireless communication signals 160 to communicate with the IMD 110, such as by using radio frequency (RF) or other telemetry signals.

Cardiac lead 108 includes a proximal end that is coupled to IMD 110 and a distal end, coupled by an electrode or electrodes to one or more portions of a heart 105. The electrodes typically deliver cardioversion defibrillation, pacing, resynchronization therapy, or combinations thereof to at least one chamber of the heart 105. IMD 110 includes components that are enclosed in a hermetically-sealed canister or "can." Additional electrodes may be located on the can, or on an insulating header, or on other portions of IMD 110, for providing unipolar pacing and/or defibrillation energy in conjunction with the electrodes disposed on or around heart 105. The lead 108 or leads and electrodes are also used for sensing electrical activity of a heart 105.

Implantable heart sound sensors are generally implantable acoustic sensors that convert the detected sounds of the heart into an electrical signal representative of the heart sounds. Typically, an acoustic sensor for an IMD includes an accelerometer mounted within the can. The accelerometer monitors heart sound vibrations along a single axis. Usually, this axis is parallel to a patient's sagittal plane and perpendicular to the patient's chest. While a single axis device results in a simple implementation, the heart sound signal components measurable along axes orthogonal to the single axis of measurement may be lost. Because heart sound vibrations along one axis may be more pronounced along a second axis, monitoring heart sounds along multiple axes may improve the signal-to-noise ratio of heart sound measurements. For example, adding signal components measured along different axes for a given heart sound may provide a stronger composite heart sound signal than measuring a single component along a particular axis. In addition to measuring heart sounds, a multi-axis acoustic sensor could measure sounds, such as cardiac murmurs.

Additionally, monitoring heart sounds along multiple axes increases the amount of useful information available for interpretation by caregivers. For example, multi-axis monitoring is believed to allow for better separation of one heart vibration from another, such as through phase angle information, direction information, and additional timing information. Multi-axis monitoring may also help separate left chamber heart sounds from right chamber heart sounds. Such multi-axis monitoring may help detect changes in the heart sounds due to cardiac synchrony or asynchrony. The multi-axis monitoring may also help separate heart sounds from other sounds such as coughing or speech sounds, or a patient's breathing.

Figure 2:
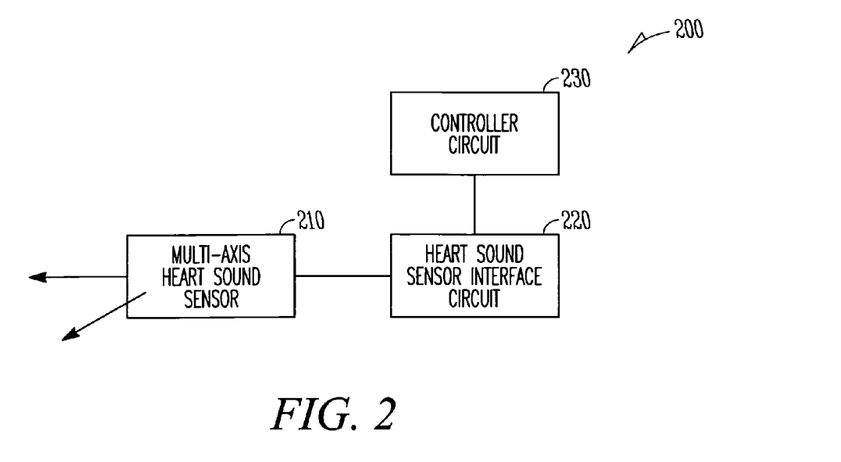
FIG. 2 shows portions of an embodiment of a system for monitoring heart sounds.

FIG. 2 shows portions of an embodiment of a system 200 for monitoring heart sounds. The system 200 includes a medical device which in turn includes at least one implantable multi-axis heart sound sensor 210, a heart sound sensor interface circuit 220 coupled to the multi-axis heart sound sensor 210, and a controller circuit 230 coupled to the heart sound sensor interface circuit 220. The multi-axis heart sound sensor 210 is operable to produce an electrical signal representative of at least one heart sound for each of at least two nonparallel axes. Such axes are typically mutually orthogonal. The heart sound sensor interface circuit 220 provides signals representative of one or more heart sounds to the controller circuit 230. In one example, the controller circuit 230 measures the signals in relation to a physiological event, such as by synchronizing the measurement to a sensed heart depolarization. An example of making heart sound measurements in relation to a heart depolarization is found in U.S. patent application Ser. No. 10/334,694 entitled, "Method and Apparatus for Monitoring of Diastolic Hemodynamics," which is hereby incorporated by reference.

In some examples, the multi-axis heart sound sensor 210 is operable to produce first, second, and third electrical signals representative of respective directional components of the heart sound for respective orthogonal first, second, and third axes. In an example, the first, second, and third axes correspond to the x, y, and z axes, with the z axis perpendicular to a patient's chest. The controller circuit 230 is operable to measure components of the heart sound that respectively correspond to each of the respective orthogonal first, second, and third axes. The term "operable" refers to the controller circuit 230 executing an algorithm or algorithms implemented by hardware, software, firmware or any combination of hardware, software or firmware. In some embodiments, the measuring is performed continuously. In some embodiments, the measuring is performed intermittently to conserve energy. In some embodiments, the controller circuit 230 includes a clock circuit and the measuring is done contingent on a certain time of day. This allows the measurements to be made while a patient is presumably in substantially the same posture or a similar posture, such as at night while a patient presumably is inactive and lying down. In some embodiments, the medical device includes a posture sensor coupled to the controller circuit 230 to determine a patient's posture when measuring the multi-axis heart sounds. Examples of posture sensors include a tilt switch and a multi-axis accelerometer.

In some examples, the heart sound sensor interface circuit 220 includes signal processing circuitry corresponding to each of the first, second, and third axes for processing the corresponding one of the first, second, and third electrical signals. This allows signal processing such as frequency-selective filtering, gain-selective amplification, or selective sensing thresholds to be used on each of the first, second, and third electronic signals. The filtering allows one heart sound signal to be separated from other heart sounds, or separated from other sources of sound such as breathing, or muscle movement. The filtering and amplification provides improvement in the signal-to-noise ratio of the measurements along each axis. In some examples, the signal processing circuitry includes filter circuits to remove components of the electrical signals associated with breathing sounds, such as lung sounds or sounds due to a patient snoring. In some examples, the controller circuit 230 includes a timing circuit, and removal of breathing sounds is synchronized with a time of day such as when a patient is likely to be sleeping.

In some examples, the controller circuit 230 includes an averaging circuit to accomplish signal processing of the signals, and the controller circuit 230 is operable to measure components of the heart sound from an ensemble or other average of multiple sampled values of like heart sound signals. One example of descriptions of systems and methods for obtaining ensemble averages of heart sound signals is found in the commonly assigned, co-pending U.S. patent application Ser. No. 10/746,874 by Siejko et al., entitled "A Third Heart Sound Activity Index for Heart Failure Monitoring," filed on Dec. 24, 2003, which is incorporated herein by reference. In some examples, the controller circuit 230 is operable to measure components of the heart sound from an ensemble ordering of multiple sampled values of like heart sound signals. In ensemble ordering, the sampled values are sorted into either ascending or descending order. The value used for the measurement is the middle (median) value. In some examples, the controller circuit 230 is operable to measure components of the heart sound from a combination of ensemble averaging and ensemble ordering of multiple sampled values of like heart sound signals. In one illustrative example, five sampled values are sorted into either ascending or descending order. The controller circuit 230 then averages the median value, the next value higher, and the next value lower than the median to determine the value used for the measurement.

In some embodiments, the controller circuit 230 combines the first, second, and third electrical signals together to produce a heart sound vector. Forming a vector of the heart sounds adds directional information to heart sound measurements. The additional phase angle and direction information from a heart sound vector are useful to a caregiver to assist in the management of patient heart disease. For patients with ischemia, contractility of a heart decreases when the heart does not receive sufficient oxygen. Insufficient oxygen to the heart is often caused by a build-up of plaque in arteries that provide oxygenated blood to the heart. The associated increase in ventricular chamber stiffness and increase in the degree of restrictive filling are correlated to an increase in loudness of S3 heart sounds. Providing directional heart sound information from multi-axis monitoring may assist a caregiver in identifying the portion of a heart that has reduced contractility. The directional information may also be useful to discriminate other sounds from heart sounds. For example, lung sounds may have a strong component along one axis that is not present along another axis.

In some examples, the controller circuit 230 deems that a condition associated with heart failure decompensation occurred when the amplitude of the measured component of at least one of the heart sound signals exceeds an amplitude threshold. In some examples, the three axes are used to define a three-dimensional threshold surface, and the controller circuit 230 deems that a condition associated with heart failure decompensation occurred when the amplitude of measured components of the heart sound signals exceeds the threshold surface.

In some embodiments, the multi-axis heart sound sensor 210 includes a multi-axis accelerometer. In some embodiments at least one axis of the multi-axis heart sound sensor 210 produces an electrical signal indicative of the patient's physical activity. This activity signal can be separated from the heart sound signal by signal processing (such as by filtering for example) and is useful in determining if the patient is inactive or active. In some examples, a circuit to interface to the accelerometer along the axis used to measure physical activity is different from the sensitivity of a circuit to interface to the accelerometer along the axis used to measure heart sounds. Different sensitivity refers to the activity sensing circuit having a different signal sensing threshold than the heart sound sensing circuit, or the activity sensing circuit providing different amplification to accelerometer signals, or the activity sensing circuit having both a different signal sensing threshold and a different amplification than the heart sound sensing circuit. Making the heart sound measurements while a patient is in a particular state of physical activity (e.g. inactive, etc . . . ) is helpful in reducing or eliminating variability from physical activity from the heart sound measurement. It also reduces noise from muscular movement of the patient.

In some embodiments, the medical device further includes a storage circuit coupled to the controller circuit 230. The storage circuit is operable to store, for each of the first, second, and third axes, information representative of the measured component of the heart sound corresponding to that one of the first, second, and third axes. In some embodiments, the medical device further includes a communication circuit to communicate with a second device to provide multi-axis heart sound information. In some examples, the controller circuit 230 is operable to communicate an indication of heart failure decompensation.

Figure 3:
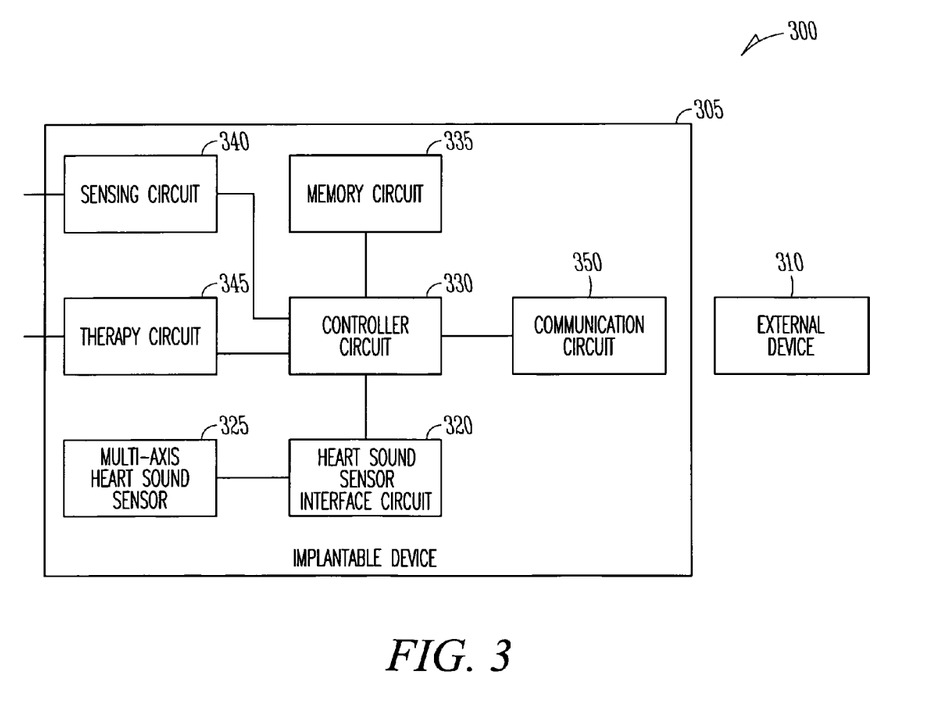
FIG. 3 shows portions of an embodiment of a system for monitoring heart sounds.

FIG. 3 shows portions of an embodiment of a system 300 for monitoring heart sounds. In this embodiment, the system 300 includes an implantable device 305 and an external device 310 operable to communicate with the implantable device 305. The implantable device 305 includes a multi-axis heart sound sensor 325 and a heart sound sensor interface circuit 320 coupled to a controller circuit 330. The multi-axis heart sound sensor 325 produces electrical signals representative of at least one heart sound for each of at least two nonparallel axes, such as at least two orthogonal axes. The controller circuit 330 is operable to measure the heart sound signal from each of the axes. The implantable device 305 also includes a memory circuit 335, a sensing circuit 340, and a therapy circuit 345. The memory circuit 335 stores heart sound measurements. The sensing circuit 340 is coupled to a cardiac lead or leads to sense one or more cardiac signals from a subject's heart. In some embodiments, the controller circuit 330 is operable to measure the heart sounds in correspondence with a sensed heart depolarization to aid in the identification of heart sounds. The heart sound signal is identified by alignment of heart sound signals to a known artifact in a sensed cardiac signal. For example, a sensed P-wave on the sensing circuit 340 helps align S1 and S2 heart sounds sensed with the multi-axis heart sound sensor 325. The therapy circuit 345 is attached to a cardiac lead or leads such as to provide cardioversion, defibrillation, pacing, resynchronization therapy, or one or more combinations thereof to at least one chamber of the heart.

The implantable device 305 further includes a communication circuit 350. The external device 310 communicates wirelessly with the implantable device 305 by using radio frequency (RF) or other telemetry signals. The implantable device 305 communicates multi-axis heart sound information to the external device 310. In some embodiments, the external device 310 is part of, or is in communication with, a computer network such as a hospital computer network or the internet. The external device 310 may be wired to the computer network or may communicate with the network wirelessly.

Figure 4A:
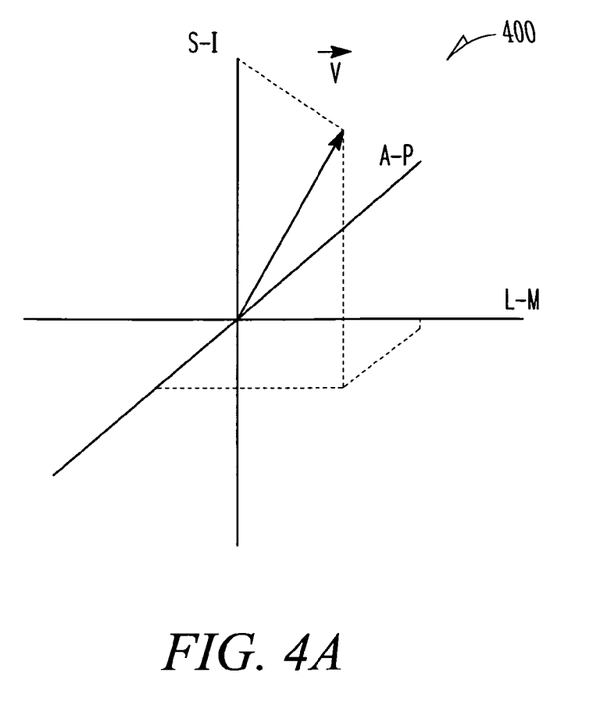
FIG. 4A shows a three dimensional display of a vector for a heart sound.

According to some embodiments, the external device 310 includes a display operable to display multi-axis heart sound information in relation to at least one of the axes. In some embodiments, the external device is operable to display at least one representation of cardiac vibrations in three dimensional space. FIG. 4A shows a three dimensional display 400 of a vector for a heart sound. Heart sound signals measured along the anterior-posterior (A-P) axis, the lateral-medial (L-M) axis, and the superior-inferior (S-I) axis are combined to create the vector. Well known trigonometric methods may be used to convert the vector display to magnitude and angle form.

Figure 4B:
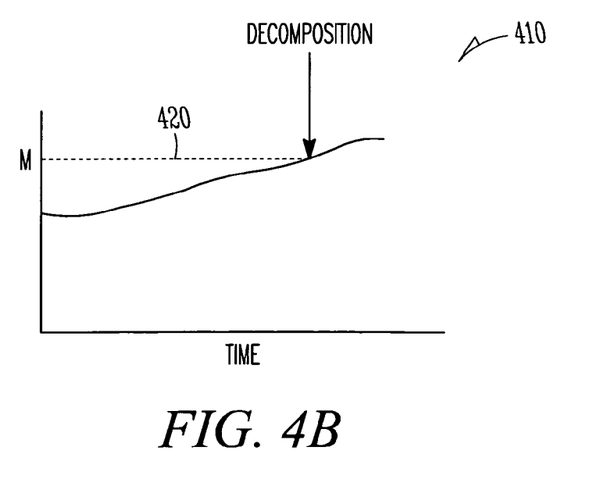
FIG. 4B shows a display of trending of a magnitude of a heart sound vector over time.

In some embodiments, the external device 310 is operable to display trending over time of multi-axis heart sound information. The trending information is useful to establish a trend indicative of a disease status of a patient or subject. This status can be an indication of worsening status or improving status. FIG. 4B shows a display 410 of trending of a magnitude of a heart sound vector |V| over time. The display 410 also shows an indication of decompensation if the vector magnitude exceeds a threshold magnitude 420. In some embodiments, the analyses are combined with one or more measurements of one or more other physiologic sensors to form a single decision as to whether to generate an alarm. For example, trending of the heart sound vector magnitude, such as displayed in FIG. 4B can be combined with trending of thoracic impedance measurements to form a decision whether to generate an alarm if both the vector magnitude exceeds a threshold and the trans-thoracic impedance is below a threshold. These analyses can be done in the implantable device 305, the external device 310, or both.

In some embodiments, the medical device 305 includes signal processing circuitry corresponding to each of the first, second, and third axes for processing the corresponding one of the first, second, and third electrical signals. In some embodiments, multi-axis heart sound information is transmitted to the external device 310 and the external device 310 is operable to perform signal processing on the information and display the processed heart sound information. In some embodiments, the external device 310 is operable to perform noise rejection signal processing, such as frequency filtering or amplification, selectively along the individual axes.

Figure 5:
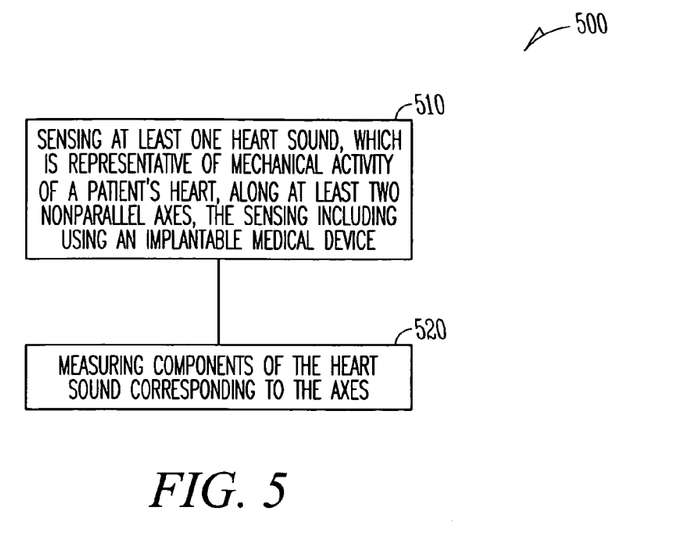
FIG. 5 shows a block diagram of an embodiment of a method for monitoring heart sounds.

FIG. 5 shows a block diagram of an embodiment of a method 500 for monitoring heart sounds. At 510, at least one heart sound is sensed that is representative of mechanical activity of a patient's heart. The heart sound includes at least one of the S1 through S4 heart sound. The heart sound is measured along at least two nonparallel axes (such as at least two orthogonal axes) and the sensing includes sensing using an implantable device. At 520, directional components of the heart sound corresponding to the axes are measured. According to some embodiments, sensing at least one heart sound includes sensing first, second, and third electrical signals representative of respective directional components of the heart sound for respective orthogonal first, second, and third axes. In some of the embodiments, the method 500 further includes combining the first, second, and third electrical signals to determine a heart sound vector. In some embodiments, the method further includes sensing a heart depolarization event using an implantable cardiac signal sensing circuit, and measuring the heart sound includes measuring the heart sound in correspondence with a sensed heart depolarization event.

In some embodiments, the method 500 further includes communicating information about the first, second, and third electrical signals to an external device. In some of the embodiments, the external device is a programmer for the implantable device. In some embodiments, the external device is in communication with a computer network. The external device can be either wired to the computer network or is a device that communicates wirelessly with the network. For example, the external device can be a repeating device that communicates with the implantable device over short distances, such as within the same room as a patient for example. The repeating device may then transmit information received from the device to the computer network. The repeating device can communicate wirelessly to the network such as by using a Wireless LAN for example, or over a communication network such as a mobile telephone network.

In some embodiments, the external device includes a display and the method 500 further includes displaying information about the components of the multi-axis heart sound measurement on the external device. In some embodiments, displaying includes displaying the information in a representation of three dimensional space. In some embodiments, displaying includes displaying the information over time in correspondence with other physiological measurements of a patient. As examples, the physiological measurements include, among others, contractility of a heart displayed as a rate of change in heart chamber pressure, patient breathing volume, and heart depolarization measured by a cardiac signal sensing circuit. In some embodiments, the method 500 further includes storing trending information about the components of the heart sound, and displaying includes displaying the trending information.

In some examples, the method 500 further includes predicting heart failure decompensation of the patient using the measured components of the heart sound. As an example, a prediction of heart failure decompensation is made from a measured increase in the amplitude of the S3 heart sound. The implantable medical device (IMD) deems that heart failure decompensation occurs when the amplitude of the S3 heart sound exceeds an amplitude threshold. In some examples, the method 500 includes providing an indication of the heart failure decompensation. In some examples, the indication is alarm, such as a buzzer or other audible indication, that heart failure decompensation occurred. In another example, the indication is communicated to an external device. In some examples, the external device is an IMD programmer and the IMD indicates that heart failure decompensation occurred by setting a status indication readable by the programmer upon a subsequent interrogation of the IMD.

Figure 6:
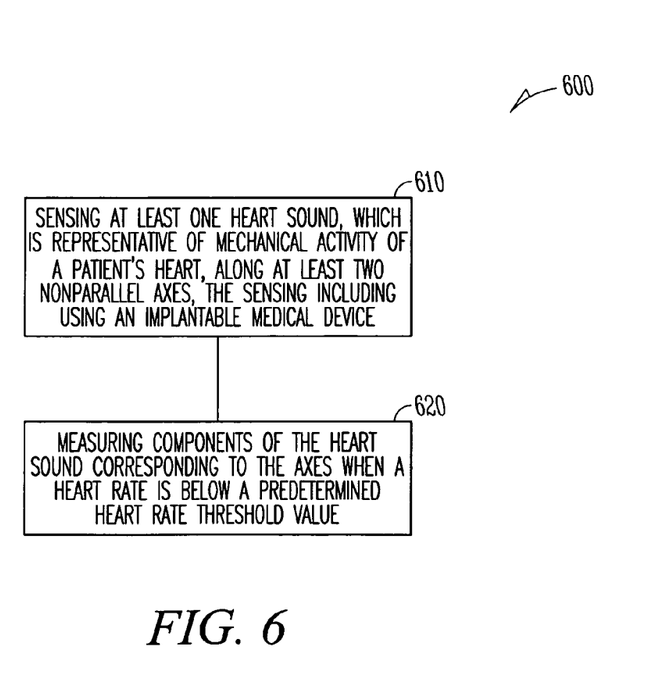
FIG. 6 shows a block diagram of an embodiment of a method for monitoring heart sounds.

Noise due to patient movement while measuring heart sounds can be reduced by taking the measurements during periods of patient inactivity. FIG. 6 shows a block diagram of another embodiment of a method 600 for monitoring heart sounds. The method 600 is similar to the method in FIG. 5 except that at 620, the heart sound components are measured when a patient's heart rate is below a predetermined heart rate threshold value. In some embodiments, the heart rate is monitored using an implantable cardiac signal sensing circuit or by monitoring the rate of occurrence of the heart sound itself. In some of the embodiments, measuring the heart sound includes measuring the heart sound according to the time of day. This allows the measurement to be taken during a time of day while the patient is likely to be resting. Measuring according to the time of day also has the advantage of taking measurements intermittently rather than continuously in order to conserve energy used by an implantable device.

Figure 7:
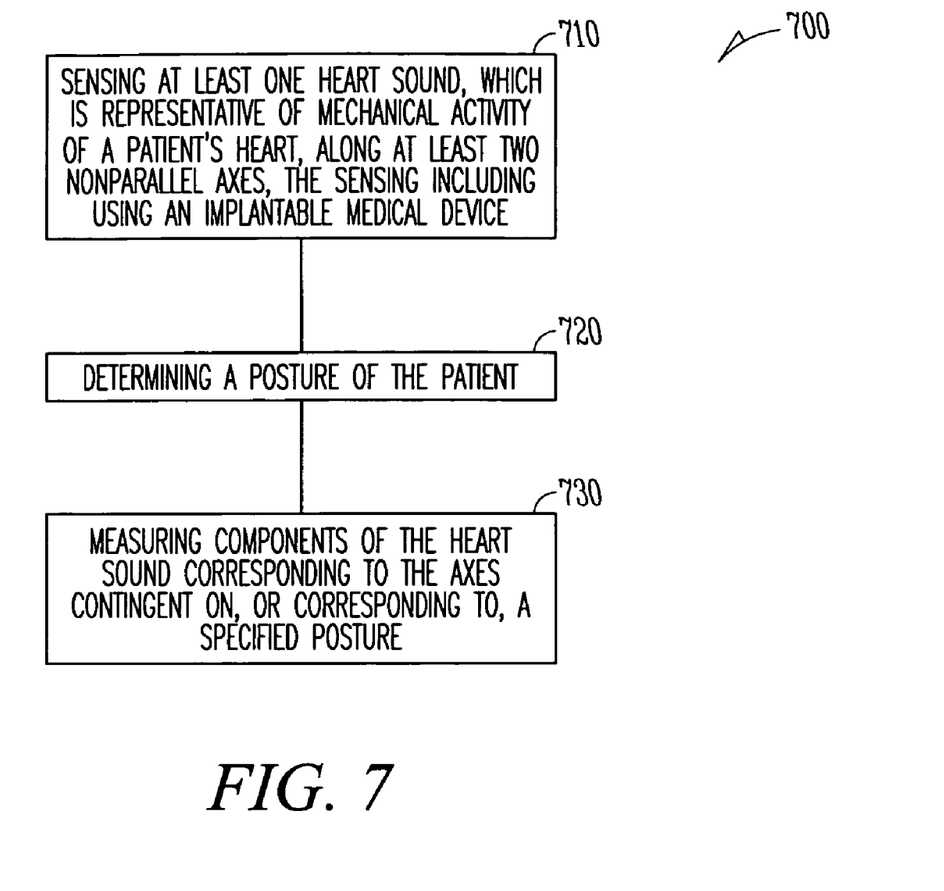
FIG. 7 shows a block diagram of an embodiment of a method for monitoring heart sounds.

FIG. 7 shows a block diagram of another embodiment of a method 700 for monitoring heart sounds. The method 700 is similar to the method in FIG. 5 except that at 720, a posture of the patient of the patient is determined. At 730, the components of the heart sound are measured contingent on, or corresponding to, a specified posture. In some embodiments, the posture is inferred from a time of day which is determined by a clock circuit. In some embodiments, a posture determination is made using a posture sensor such as a tilt switch or multi-axis accelerometer. In some embodiments, a multi-axis accelerometer is used to both determine posture and sense heart sounds. Filtering or signal processing can be used to separate the electrical signal components due to movement from the electrical signal components due to heart sounds.

The additional phase angle information, direction information, and timing information from multi-axis monitoring of heart sounds provides useful information to a caregiver to assist in the management of patient heart disease. Multi-axis heart sound monitoring may also assist in placement of electrodes that are part of a cardiac signal sensing circuit. Improper or ineffective electrode placement would be manifested by low contractility shown by the measured heart sounds. Properly placing the electrodes would then be manifested by increased contractility as indicated by the heart sounds.

The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations, or variations, or combinations of various embodiments. Combinations of the above embodiments, and other embodiments not specifically described herein, will be apparent to those of skill in the art upon reviewing the above description.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own.

What is claimed is:

1. A system comprising:
   a medical device including:
   at least one implantable multi-axis heart sound sensor, configured to produce a first electrical signal and a second electrical signal representative of respective components for respective first and second non-parallel axes of at least one heart sound, the heart sound associated with mechanical activity of a patient's heart; and
   a controller circuit, coupled to the heart sound sensor, the controller circuit configured to:
   measure components of the heart sound that respectively correspond to each of the axes;
   use the components to produce a heart sound vector representative of the heart sound, wherein the heart sound vector includes heart sound magnitude and heart sound directional information; and
   use the heart sound directional information to provide a physiological diagnostic indication.

2. The system of claim 1, the medical device further including a storage circuit coupled to the controller circuit, the storage circuit operable to store, for each of the first and second axes, information representative of the measured component of the heart sound corresponding to that one of the first and second axes.

3. The system of claim 1, further including a heart sound sensor interface circuit, coupled to the heart sound sensor, the heart sound sensor interface circuit including signal processing circuitry corresponding to each of the first and second axes for processing the corresponding electrical signal.

4. The system of claim 3, wherein the signal processing circuitry includes filter circuits to remove components of the electrical signals associated with breathing sounds.

5. The system of claim 1, wherein the multi-axis heart sound sensor is operable to produce first, second, and third electrical signals representative of respective components of the heart sound for respective orthogonal first, second, and third axes, and wherein the controller circuit is operable to measure components of the heart sound that respectively correspond to each of the respective orthogonal first, second, and third axes.

6. The system of claim 1, wherein the controller circuit is operable to combine the first, second, and third electrical signals together to produce a heart sound vector including heart sound directional information.

7. The system of claim 1, wherein the multi-axis heart sound sensor includes a multi-axis accelerometer.

8. The system of claim 7, wherein at least one axis of the multi-axis heart sound sensor produces an electrical signal indicative of the patient's physical activity.

9. The system of claim 1, wherein the medical device further includes a communication circuit, wherein the system further includes a second device operable to communicate with the medical device to obtain multi-axis heart sound information, and wherein the second device is in communication with a computer network.

10. The system of claim 1, wherein the medical device further includes a communication circuit and wherein the system further includes a second device operable to communicate with the medical device, wherein the second device includes a display, and wherein the second device is operable to display the multi-axis heart sound information in relation to at least one of the axes.

11. The system of claim 10, wherein the second device is operable to display trending over time of the multi-axis heart sound information.

12. The system of claim 11, wherein the trending is combined with one or more measurements of one or more other physiologic sensors to form a single decision as to whether to generate an alarm.

13. The system of claim 11, wherein the second device is operable to perform signal processing on the multi-axis heart sound information prior to trending and to display processed heart sound information.

14. The system of claim 10, wherein the medical device is operable to communicate an alarm indicating heart failure decompensation.

15. The system of claim 1, wherein the controller circuit is operable to measure components of the heart sound using an average of electrical signals.

16. The system of claim 1, wherein the controller circuit is operable to measure components of the heart sound using an ordering of electrical signals.

17. The system of claim 1, wherein the controller circuit is further operable to deem that heart failure decompensation occurred when an amplitude of the measured component of the heart sounds exceeds a threshold amplitude and wherein the controller circuit is operable to provide an indication of the heart failure decompensation.

18. The system of claim 1, wherein the physiological diagnostic indication includes an indication of a change in heart contractility.

19. The system of claim 1, wherein the physiological diagnostic indication includes an indication of heart failure decompensation.

20. The system of claim 1, wherein the implantable medical device further includes a communication circuit and wherein the system further includes a second device configured to communicate with the medical device, wherein the second device is configured to trend a heart sound vector, including the directional information, to detect an indication of heart failure.

21. A method comprising:
sensing at least one heart sound, which is representative of mechanical activity of a patient's heart, along first and second nonparallel axes, the sensing including using an implantable medical device and producing a first electrical signal and a second electrical signal representative of respective components for the respective first and second non-parallel axes;
measuring components of the heart sound that respectively correspond to each of the axes;
using the components to produce a vector representative of the heart sound, wherein the heart sound vector includes heart sound magnitude and heart sound directional information; and
using the heart sound directional information to provide a physiological diagnostic indication.

22. The method of claim 21, wherein sensing at least one heart sound includes sensing first, second, and third electrical signals representative of respective components of the heart sound for respective orthogonal first, second, and third axes.

23. The method of claim 22, further including combining the first, second, and third electrical signals to determine a heart sound vector.

24. The method of claim 21, further including communicating information about the measured components in correspondence with the axes to an external device.

25. The method of claim 24, further including displaying on the external device information about the components of the multi-axis heart sound measurement.

26. The method of claim 21, further including storing trending information about the components of the heart sound.

27. The method of claim 21, further including displaying the trending information.

28. The method of claim 21, further including monitoring a heart rate, and wherein the measuring the components of the heart sound includes measuring the components of the heart sound when the heart rate is below a predetermined heart rate threshold value.

29. The method of claim 21, further including determining a posture of the patient, and wherein the measuring the components of the heart sound includes measuring the components of the heart sound contingent on or corresponding to a specified posture.

30. The method of claim 21, further including determining a time of day, and wherein the measuring the heart sound includes measuring the heart sound according to the time of day.

31. The method of claim 21, further including sensing a heart depolarization event using an implantable cardiac signal sensing circuit, and wherein the measuring the heart sound includes measuring the heart sound in correspondence with a sensed heart depolarization event.

32. The method of claim 21, further including:
predicting heart failure decompensation of the patient using the measured components of the heart sound; and
providing an indication of the heart failure decompensation.

33. The method of claim 32, wherein predicting heart failure decompensation includes detecting that an amplitude of a heart sound exceeds a threshold amplitude.

* * * * *

UNITED STATES PATENT AND TRADEMARK OFFICE
CERTIFICATE OF CORRECTION

PATENT NO. : 7,424,321 B2  
APPLICATION NO. : 11/135985  
DATED : September 9, 2008  
INVENTOR(S) : Wariar et al.

It is certified that error appears in the above-identified patent and that said Letters Patent is hereby corrected as shown below:

On the title page, item (75), in "Inventors", in column 1, line 5, after "(US)" insert -- ; Keith R. Maile, New Brighton, MN (US) --.

On the title page, item (74), in "Attorney, Agent, or Firm", in column 2, line 2, delete "Wuessner," and insert -- Woessner, --, therefor.

Signed and Sealed this

Fourth Day of May, 2010

David J. Kappos
*Director of the United States Patent and Trademark Office*